US00PP18029P2

(12) United States Plant Patent
Jonkers et al.

(10) Patent No.: US PP18,029 P2
(45) Date of Patent: Sep. 11, 2007

(54) ***IMPATIENS* PLANT NAMED 'SILTE ORANSAR'**

(50) Latin Name: *Impatiens walleriana*
Varietal Denomination: Silte Oransar

(75) Inventors: Johanna B. Jonkers, Andijk (NL); Erik Smit, Enkhuizen (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/410,636

(22) Filed: Apr. 25, 2006

(51) Int. Cl.
*A01H 5/00* (2006.01)

(52) U.S. Cl. ..... Plt./317
(58) Field of Classification Search ..... Plt./317
See application file for complete search history.

*Primary Examiner*—Kent Bell
(74) *Attorney, Agent, or Firm*—Jondle & Associates, P.C.

(57) ABSTRACT

A new *Impatiens* plant particularly distinguished by medium-sized, double orange and while flowers borne well-above the foliage, medium-green foliage with round leaves, an early flowering response, floriferous throughout the summer and a medium-sized, bushy and moderately tight plant habit, is disclosed.

1 Drawing Sheet

Genus and species: *Impatiens walleriana.*
Variety denomination: 'Silte Oransar'.

BACKGROUND OF THE NEW PLANT

The present invention comprises a new and distinct cultivar of *Impatiens,* botanically known as *Impatiens walleriana,* and hereinafter referred to by the cultivar name 'Silte Oransar'. The new cultivar originated from a hybridization made in May 2003 in Andijk, The Netherlands. The female parent was the proprietary red-star-flowered *Impatiens* plant 'ID03-20-7' (unpatented), while the male parent was the proprietary salmon-star-flowered *Impatiens* plant 'ID03-30-6' (unpatented). The seeds produced by the hybridization were sown Andijk, Netherlands in October 2003. A single plant selection was chosen for further evaluation and for asexual propagation in December 2003 in Andijk, The Netherlands.

The new cultivar was created in 2003 in Andijk, The Netherlands and has been asexually reproduced repeatedly by vegetative cuttings and tissue culture in Andijk, The Netherlands and Hillscheid, Germany over a two-year period. 'Silte Oransar' has not been observed under all possible environmental conditions. The present invention has been found to retain its distinctive characteristics through successive asexual propagations.

Plant Breeder's Rights for this cultivar were applied for in Canada on Oct. 17, 2005 and with the European Union on Nov. 18, 2005.

SUMMARY OF THE INVENTION

The following are the most outstanding and distinguishing characteristics of this new cultivar when grown under normal horticultural practices in Andijk, The Netherlands, and Hillscheid, Germany.

1. Medium-sized orange and white, bi-colored double flowers borne well-above the foliage;
2. Medium-green foliage with round leaves;
3. A medium-sized, bushy and moderately tight plant habit;

4. An early flowering response; and
5. Floriferous throughout the summer.

DESCRIPTION OF PHOTOGRAPH

This new *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 10-weeks old, grown in a greenhouse in Hillscheid, Germany in late May 2005.

DESCRIPTION OF THE NEW CULTIVAR

The following detailed descriptions set forth the distinctive characteristics of 'Silte Oransar'. The date which defines these characteristics were collected from asexual reproductions carried out in Hillscheid, Germany. The plant history was taken in mid September on 9- to 10-week old un-pinched plants which had been planted as rooted cuttings in 12-cm pots in mid-July 2005 and grown in a greenhouse at a minimum temperature of 21° C. Color readings were taken under natural light in the greenhouse. Color references are primarily to the R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens walleriana* Hook.
*Common name.*—*Impatiens.*

Parentage:
*Female parent.*—'ID03-20-7' a proprietary red-star (bi-color) flowered *Impatiens* plant (unpatented).
*Male parent.*—'ID03-30-6' a proprietary salmon-star (bi-color) flowered *Impatiens* plant (unpatented).

Growth:
*Growth and branching habit.*—Medium vigor, a medium-sized, round, bushy, moderately tight and well-branched plant habit; pinching of the terminal apices may lead to a more evenly mounded plant habit.

*Height.*—22.4 cm.

*Width.*—14.5 cm.

*Propagation.*—Terminal tips for cuttings.

*Time to produce a finished flowering plant.*—8 weeks for a 12-cm pot.

*Time to initiate and develop roots.*—18 days or less at 22° C.

Branches:

*Average number.*—7.7.

*Length of main branches.*—18 cm to 21 cm.

*Internode length.*—4 cm to 5 cm.

*Diameter of branches* (*at midpoint*).—0.5 cm to 0.8 cm.

*Stem color.*—RHS 147D at the tips, RHS 144C at the middle part, with RHS 184D (weak reddish) lines or dots and infused with RHS 184D at the nodes.

Leaves:

*Arrangement.*—Alternate and partly in whorls at the flowering stems.

*Size.*—Length: Up to 8.5 cm. Width: 4.0 cm.

*Shape.*—Elliptical to rhomboid.

*Margin.*—Weakly serrate or crenate, ciliated (short).

*Apex.*—Acuminate.

*Base.*—Acute.

*Color* (*mature leaves*).—Upper surface: RHS 137C (medium green). Lower surface: RHS 138B, with a pattern of RHS 197A (grayish) or RHS 186D (weakly purple) spots.

*Color* (*immature leaves*).—Upper surface: Near RHS 137C. Lower surface: Mainly RHS 138B.

*Texture.*—Glabrous.

*Venation color.*—Upper surface: Indistinct. Lower surface: RHS 147C.

*Petioles.*—Length: 1.5 cm. Diameter: 0.3 cm to 0.4 cm. Color: Upper surface: RHS 145D. Lower surface: RHS 145C to RHS 145D. Texture: glabrous.

Flower buds:

*Shape.*—Nearly round.

*Size.*—Length: Up to 1.7 cm. Diameter: Up to 1.7 cm.

*Color at tight bud.*—RHS 52B (pink) and partly RHS 49D or RHS 155A (whitish).

Inflorescence:

*Blooming habit.*—7 to 8 weeks after planting of rooted cuttings.

*Inflorescence type.*—Inflorescences appear solitary in the leaf axiles of the upper nodes of the stems.

*Number of flowers per node.*—2 to 4, in various stages of development.

*Flowering season.*—Continuously flowers, mainly from March to October, depending on light intensity.

*Lastingness of the individual blooms to the plant.*—5 to 7 days (at 18° C. in a greenhouse in the spring).

*Fragrance.*—None.

*Peduncle.*—Color: RHS 166D at the base to RHS 144B at the upper part. Size: Length: Variable, about 4.5 cm to 8.5 cm. Diameter: Lower end: 0.3 cm. Upper end: 0.15 cm. Texture: Flexible, glabrous.

Flowers:

*Form of corolla.*—Double-type.

*Shape of corolla.*—Initially rose-bud like with the outer petals opening very wide.

*Corolla size.*—Diameter: 3.6 cm to 3.8 cm. Depth: 1.5 cm to 2.0 cm.

*Number of flowers.*—17 to 20.

Petals:

*Shape.*—Mostly obovate, banner petal is cordate.

*Apex.*—Rounded or emarginate.

*Base.*—Attenuate.

*Margin.*—Entire.

*Size.*—Length: 1.7 cm to 2.0 cm. Width: Mostly 1.8 cm. Banner petal width: Up to 2.3 cm.

*Color.*—General color description: Bi-colored, orange with white stripes. Upper surface: RHS 43B to RHS 43C. Lower surface: RHS 52B.

*Markings.*—A wide central stripe on each petal that is whiter than RHS 155D.

*Texture.*—Smooth, satiny.

Spur:

*Shape.*—Curved, downward directed.

*Color.*—RHS 145B (pale green).

*Size.*—Length: 3.4 cm. Diameter: 0.2 cm at the flower base.

Reproductive organs:

*Stamens.*—Not observed.

*Pistils.*—Style and stigma: Not developed. Ovary: 5-called. Ovary length: 0.6 cm. Ovary color: RHS 143A (green).

Fruit and seed set: No seed set observed.

Disease and insect resistance: No particular resistance or susceptibility has been observed.

COMPARISON WITH PARENTAL AND COMMERCIAL CULTIVARS

'Silte Oransar' differs from the female parent 'ID03-20-7' (unpatented) by having orange and white bi-colored, double flowers, while 'ID03-20-7' has red-star, single flowers.

'Silte Oransar' differs from the male parent 'ID03-30-5' (unpatented), by having orange and white bi-colored, double flowers, while 'ID03-30-6' has salmon-star, single flowers.

'Silte Oransar' differs from the commercial cultivar 'Didi Orange Two' (U.S. Plant Pat. No. 15,840) by having medium-sized, bi-colored orange and white flowers, while 'Didi Orange Two' has larger, fairly uniform, deeper orange flowers. Additionally, the plant habit of 'Silte Oransar' appears to be wider the than plant habit of 'Didi Orange Two'.

'Silte Oransar' differs from the commercial cultivar 'Didi Salmon Two' (U.S. Plant Pat. No. 15,908) by having smaller flowers with fewer petals than 'Did Salmon Two'. Additionally, 'Didi Salmon Two' has tighter rose-shaped flowers than 'Silte Oransar'.

I claim:

1. A new and distinct cultivar of *Impatiens* plant as shown and described herein.

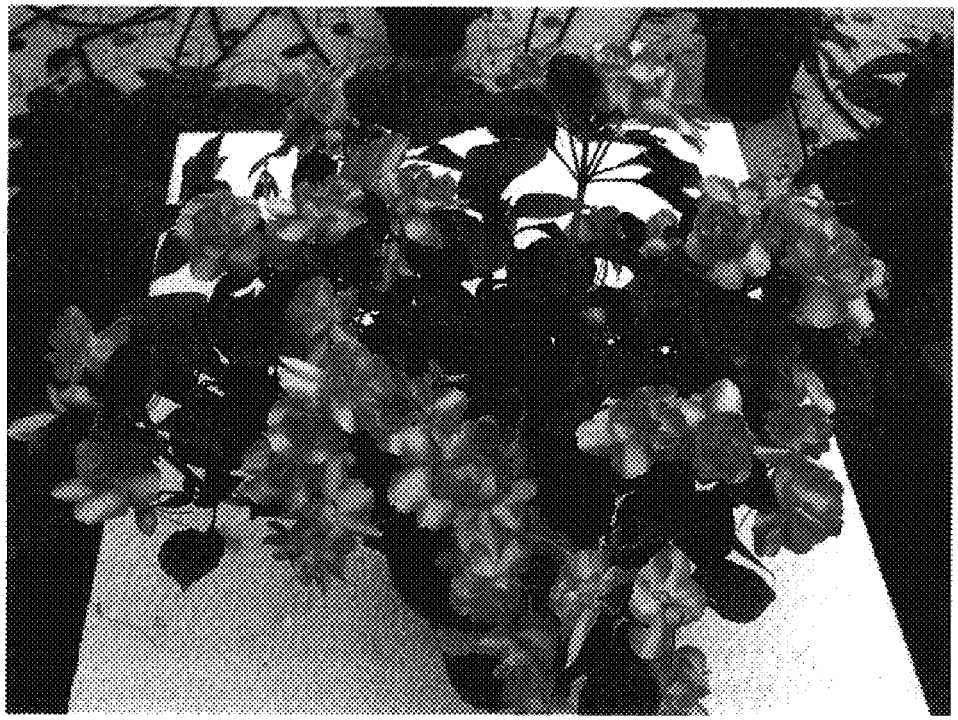

* * * * *